US 6,733,129 B2

(12) United States Patent
Masaki

(10) Patent No.: US 6,733,129 B2
(45) Date of Patent: May 11, 2004

(54) OPHTHALMOLOGIC APPARATUS AND AUTO-ALIGNMENT METHOD

(75) Inventor: Toshifumi Masaki, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 123 days.

(21) Appl. No.: 10/107,467

(22) Filed: Mar. 26, 2002

(65) Prior Publication Data

US 2002/0159028 A1 Oct. 31, 2002

(30) Foreign Application Priority Data

Mar. 29, 2001 (JP) .................................. 2001-096020

(51) Int. Cl.⁷ ............................. A61B 3/14; A61B 3/00
(52) U.S. Cl. ..................... 351/208; 351/206; 351/246
(58) Field of Search ............................. 351/200, 205, 351/206, 208, 210, 211–216, 221, 246; 128/898; 600/558

(56) References Cited

U.S. PATENT DOCUMENTS

| | | | |
|---|---|---|---|
| 4,995,393 A | | 2/1991 | Katsuragi et al. ............. 128/648 |
| 5,302,979 A | | 4/1994 | Maeda et al. ................. 351/212 |
| 5,436,679 A | * | 7/1995 | Ohtsuka et al. ............... 351/206 |
| 5,532,769 A | * | 7/1996 | Miwa et al. ................... 351/205 |
| 5,644,375 A | * | 7/1997 | Suzuki ........................ 351/208 |
| 5,689,325 A | * | 11/1997 | Isogai et al. ................. 351/208 |
| 5,696,573 A | * | 12/1997 | Miwa .......................... 351/208 |
| 5,757,461 A | * | 5/1998 | Kasahara et al. .............. 351/206 |
| 5,822,034 A | | 10/1998 | Shimashita et al. ........... 351/212 |
| 5,844,659 A | | 12/1998 | Isogai ........................ 351/208 |
| 5,905,562 A | * | 5/1999 | Isogai et al. ................. 351/208 |
| 5,975,698 A | * | 11/1999 | Iijima ......................... 351/208 |
| 6,145,990 A | * | 11/2000 | Uchida ........................ 351/221 |
| 6,296,358 B1 | * | 10/2001 | Cornsweet et al. ............ 351/206 |
| 6,361,168 B1 | * | 3/2002 | Fujieda ....................... 351/208 |
| 6,409,343 B1 | * | 6/2002 | Uchida ........................ 351/208 |
| 6,494,577 B2 | * | 12/2002 | Iwanaga ...................... 351/208 |
| 2002/0018179 A1 | * | 2/2002 | Hayashi et al. ............... 351/208 |
| 2003/0139687 A1 | * | 7/2003 | Abreu ......................... 600/558 |

FOREIGN PATENT DOCUMENTS

EP 0 820 720 A1 1/1998

OTHER PUBLICATIONS

Patent Abstract of Japan, vol. 1 1997 No. 07 Jul. 31, 1997 & JP 09 066027 A Mar. 11, 1997 (Canon K.K.).
European Search Report dated Jul. 5, 2002.

* cited by examiner

Primary Examiner—Dennis W. Ruhl
Assistant Examiner—John R Sanders
(74) Attorney, Agent, or Firm—Morgan & Finnegan, L.L.P.

(57) ABSTRACT

An aligning method for an ophthalmologic apparatus including a measurement optical system for measuring the eyes of an object to be examined and an illumination system for illuminating the eyes with extrinsic eye light is disclosed. When a reflected cornea image can be detected by irradiating an eye of the object with alignment light, alignment of the measurement optical system is executed on the basis of the reflected cornea image. If no reflected cornea image of the alignment light can be detected, a reflected cornea image formed by the extrinsic eye light is detected, and alignment of the measurement optical system is executed on the basis of the reflected cornea image formed by the extrinsic eye light. Thereafter, the reflected cornea image is detected again.

15 Claims, 7 Drawing Sheets

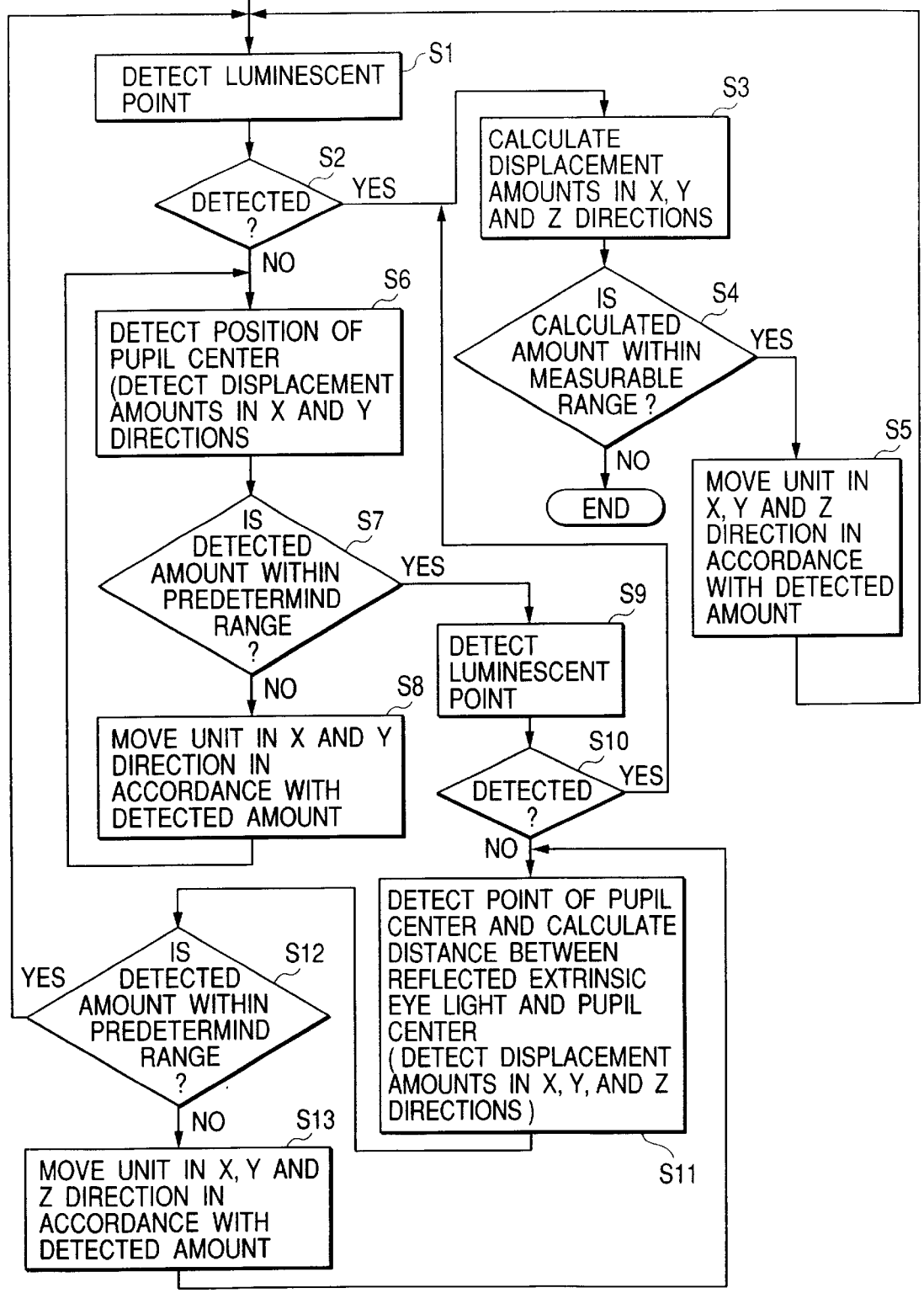

OPHTHALMOLOGIC APPARATUS AND AUTO-ALIGNMENT METHOD

CROSS REFERENCE TO RELATED APPLICATIONS

The present application claims priority from and the benefit of Japanese Patent Application No. 096020/2001, filed Mar. 29, 2001.

BACKGROUND OF THE INVENTION

1. Field of the Invention

The present invention relates to an ophthalmologic apparatus which allows easy alignment of a measurement optical system with respect to a patient's eye to be examined, and an auto-alignment method for the apparatus.

2. Related Background Art

An ophthalmologic apparatus having an auto-alignment function is known.

Such an ophthalmologic apparatus can perform so-called auto-alignment, in which a light beam is projected on the cornea of an eye to be examined, and the alignment state of the optical axis of the measurement optical system with respect to the eye is detected by detecting the reflected light through a light-receiving element, thereby automatically setting the relation between the eye and the optical axis of the measurement optical system to have a predetermined relationship on the basis of the alignment state.

The above auto-alignment function exhibits a narrow range in which reflected light from the cornea can be detected by the light-receiving element; there is a room for improvement.

When the measurement optical system in the initial state falls outside a detectable range in which auto-alignment can be done, and no reflected light can be detected, an operator needs to manually align the measurement optical system (measurement unit) with the eye until the optical system falls within the detectable range.

Such operation is a burden for the operator of this apparatus, and hinders quick measurement. One of measures against this problem is to widen the detectable range of alignment by using a large-aperture light-receiving lens or a sensor having a large light-receiving surface. An increase in apparatus size, however, will lead to increases in cost and complexity.

According to another approach, the ophthalmologic apparatus disclosed in Japanese Patent Application Laid-Open No. 9-66027 is aimed at widening the detectable ranges in the up-and-down and right-and-left (X and Y) directions by performing alignment detection on the basis of a virtual image of an anterior illumination light source on an eye to be examined. However, since no special optical system for alignment detection is used, high detection precision cannot be ensured. In addition, according to the structure of this apparatus, the detectable range for alignment in the forward-and-backward (Z) direction cannot be broadened.

SUMMARY OF THE INVENTION

It is an object of the present invention to provide a method and ophthalmologic apparatus which allow high-precision auto-alignment in a wide range.

In order to achieve the above object, according to an aspect of the present invention, there is provided an ophthalmologic apparatus comprising a movable measurement unit which includes a measurement optical system for measuring an eye to be examined, a first light source which irradiates the eye with light from a direction different from an optical axis of the measurement optical system, a second light source which irradiates the eye with light from an optical axis direction of the measurement optical system, an image pickup device to obtain an image of the eye, a first detection system which detects an aligned state of the measurement unit with the eye by obtaining a position of a reflected cornea image of the second light source on the basis of the image picked up by the image pickup device, and a second detection system which detects an aligned state of the measurement unit with the eye by detecting a position of the reflected cornea image of the first light source on the basis of the image picked up by the image pickup device.

According to another aspect of the present invention, there is provided an auto-alignment method for an ophthalmologic apparatus including a measurement optical system which measures an eye to be examined, and an illumination system which illuminates the eye with extrinsic eye light, comprising the detection step of irradiating the eye with a light beam through the measurement optical system, and detecting a reflected cornea image of the light beam, the aligning step of, when a reflected cornea image can be detected in the detection step, aligning the measurement optical system with the eye on the basis of a position determined based on the reflected cornea image, and the step of, when no reflected cornea image can be detected in the detection step, detecting a reflected cornea image by illumination of the extrinsic eye light, aligning the measurement optical system in accordance with the detected reflected cornea image, and then performing the detection step again.

The above and other objects, features, and advantages of the present invention will be apparent from the following detailed description in conjunction with the accompanying drawings and the appended claims.

BRIEF DESCRIPTION OF THE DRAWINGS

FIG. 9 is a flow chart showing a procedure for auto-alignment.

DETAILED DESCRIPTION OF THE PREFERRED EMBODIMENT

The present invention will be described in detail below with reference to the embodiment shown in the accompanying drawings.

An eye refractive power measurement apparatus as an ophthalmologic apparatus will be exemplified. Note that the ophthalmologic apparatus to which the present invention can be applied is not limited to this but can be applied to various devices that demand precise alignment of an optical system with the eye, e.g., corneal measurement apparatuses for measuring various types of cornea information, optometers, eye fundus cameras, and blood flowmeters.

Figure 1:
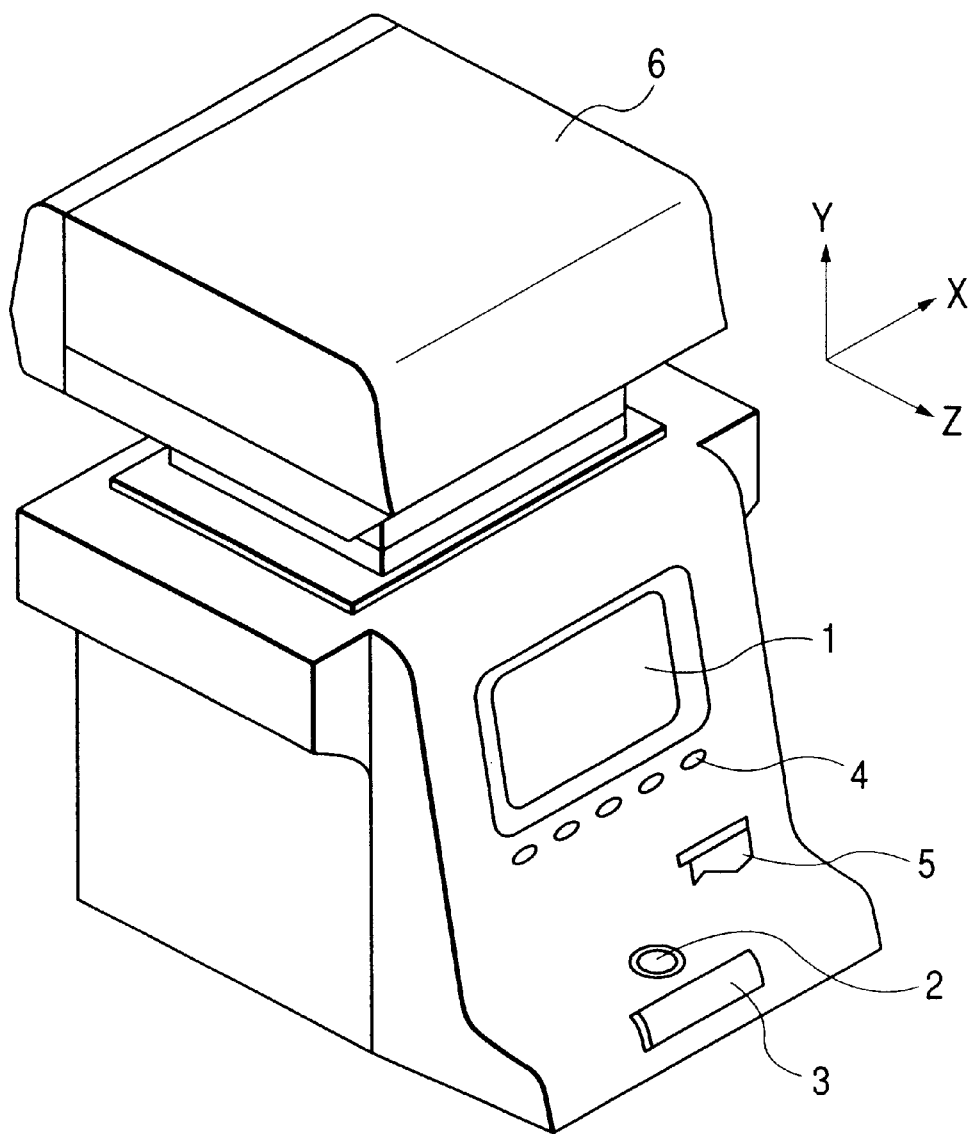
FIG. 1 is a perspective view of an ophthalmologic apparatus according to an embodiment.

FIG. 1 is a schematic view of an apparatus according to this embodiment. A display 1 (liquid crystal display or CRT) for displaying a measured value, an image of an eye of a patient, and the like or displaying/providing a user interface used for various settings is mounted on the surface of the apparatus on which an operator performs operation. In addition, a track ball 2 and roller 3 which are input devices for manually aligning a measurement unit with the eye, a switch panel 4 (having a printer print switch, measurement start switch, selecting/setting switch, and the like), and a printer 5 are arranged on this surface. The face of the patient is fixed on a face rest (not shown) on the opposite side to the surface on which the operator performs operation, and an eye E is set in front of the optical system of the measurement unit.

Figure 2:
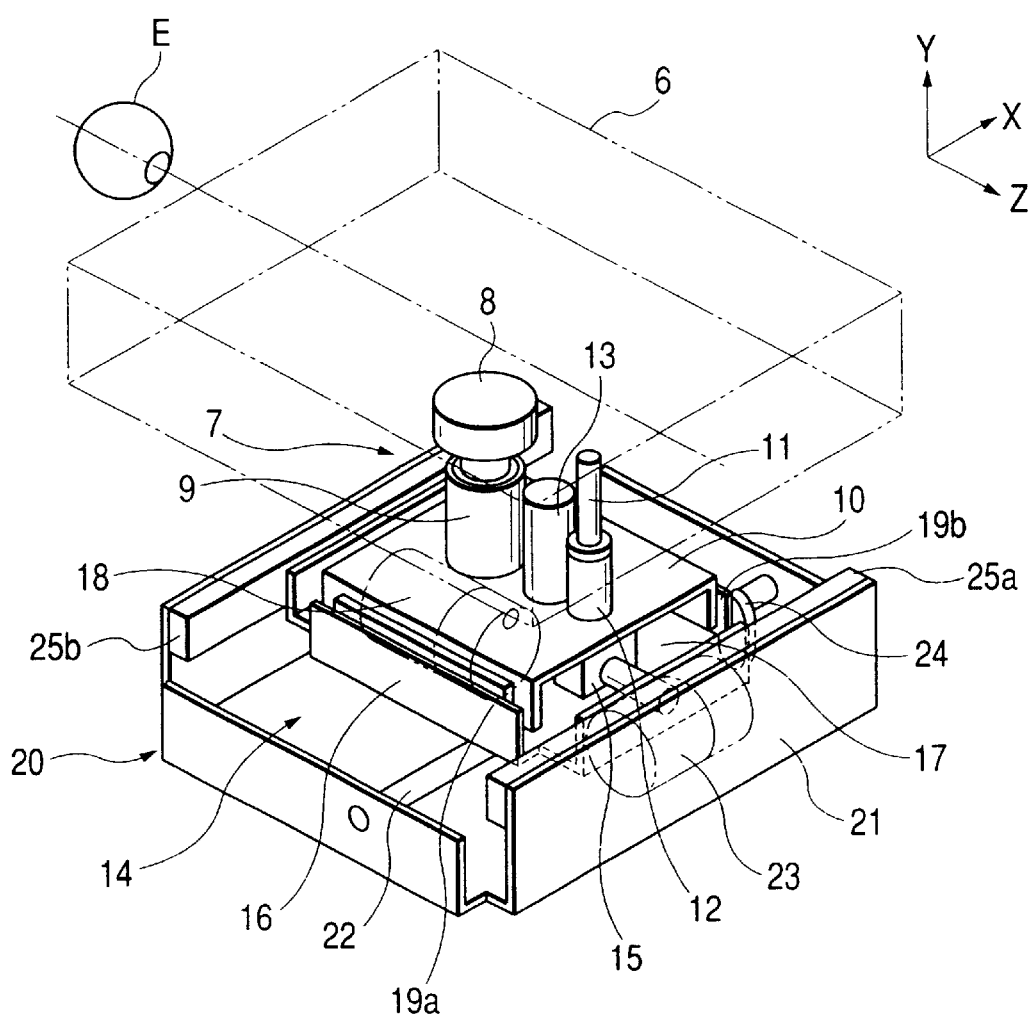
FIG. 2 is a perspective view showing the structure of a driving mechanism for driving the measurement unit.

FIG. 2 is a perspective view showing a driving mechanism for automatically aligning a measurement unit 6 with the eye E. This apparatus includes the measurement unit 6 incorporating an optical system for measurement. The measurement unit 6 is moved in the up-and-down direction (Y direction) within the range of about 30 mm by an up and down driving mechanism 7 for moving the unit in the up-and-down direction. The measurement unit 6 is supported on a support 8 and joined to a support 9 incorporating a direct-acting ball bearing and a feed screw for vertical movement. The support 9 is fixed on a base 10. A fitting support 11 protrudes from below the measurement unit 6 to restrict the rotation of the measurement unit 6 about the central axis of the support 8 and is fitted in a direct-acting bearing 12 fixed to the base 10. An up and down motor 13 is placed between the support 9 and the direct-acting bearing 12 to rotate the feed screw of the support 9 via a belt on the lower surface of the base 10. Therefore, as the motor 13 rotates clockwise and counterclockwise, the measurement unit 6 moves up and down. Limit switches (not shown) at the two ends of a stroke in the up-and-down direction detect movement limits. An encoder capable of counting pulses is coaxially placed on the motor 13. A photocoupler for detecting the encoder is placed on the lower surface of the base 10.

A forward and backward mechanism 14 drives the measurement unit 6 in the forward-and-backward direction (Z direction). A female thread nut 15 is fixed to the lower surface of the base 10. The female thread nut 15 is threadably engaged with a feed screw 17 supported on a base 16. The feed screw is coupled to a forward and backward motor 18 via a coupling. Direct-acting guide rails 19a and 19b are arranged on the left and right side surfaces of the base 10; the movable and fixed sides are respectively joined to the base 10 and base 16. As the forward and backward motor 18 rotates clockwise and counterclockwise, the measurement unit 6 including the up and down driving mechanism 7 moves forward and backward within the range of about 40 mm. Limit switches (not shown) at the two ends of a stroke in the forward-and-backward direction detect movement limits. An encoder capable of counting pulses is coaxially placed on the forward and backward motor 18. A photocoupler for detecting the encoder is placed on the upper surface of the base 10.

A right and left driving mechanism 20 drives the measurement unit 6 in the right-and-left direction (X direction). A female thread nut is fixed to the lower surface of the base 16. The female thread nut is threadably engaged with a feed screw 22 supported on a base 21. The feed screw 22 is coupled to a right and left motor 23 via a belt 24. Direct-acting guide rails 25a and 25b are arranged on the front and rear surfaces of the base 16; the movable and fixed sides are respectively joined to the base 16 and base 21. As the right and left motor 23 rotates clockwise and counterclockwise, the measurement unit 6 including the up and down driving mechanism 7 and forward and backward mechanism 14 moves in the right-and-left direction within the range of about 90 mm. Limit switches (not shown) at the two ends of a stroke in the right-and-left direction detect movement limits. An encoder capable of counting pulses is coaxially placed on the right and left motor 23. A photocoupler for detecting the encoder is placed on the upper surface of the base 21.

As described above, the measurement unit 6 is moved by the up and down driving mechanism 7 (Y direction), forward and backward mechanism 14 (Z direction), and right and left driving mechanism 20 (X direction) in the respective directions in three dimensions with respect to the eye E. Therefore, this apparatus can cope with objects with various sizes, from children to adults. When an object fixes his/her face on the face rest, the measurement unit is aligned with an eye of the object.

Figure 3:
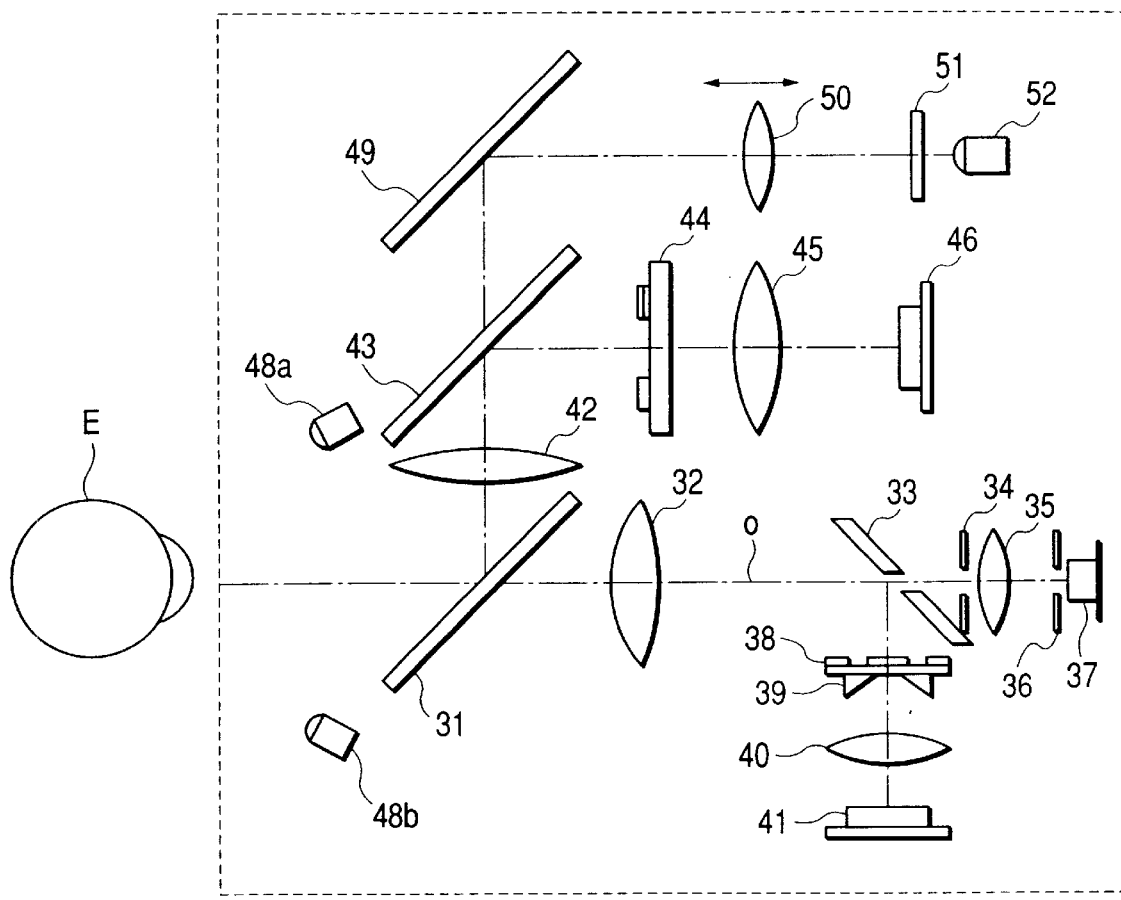
FIG. 3 is a view showing the internal optical arrangement of the measurement unit.
Figure 5:
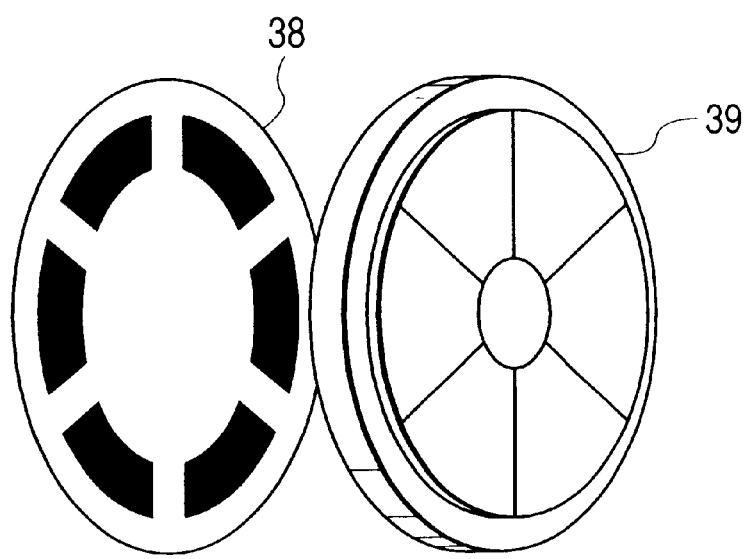
FIG. 5 is a view showing the arrangement of a prism stop.

FIG. 3 shows the arrangement of the optical system in the measurement unit 6. A dichroic mirror 31 for totally reflecting visible light and partially reflecting a light beam having a wavelength of 880 nm, an objective lens 32, an apertured mirror 33, a stop 34, a projection lens 35, a projection stop 36, and a measurement light source 37 with a wavelength of 880 nm are arranged on a central axis O of the measurement unit 6 to be aligned with the optical axis of the eye E. A 6-piece stop 38, 6-piece prism 39, light-receiving lens 40, and two dimensional image pickup element (two dimensional CCD) 41 are arranged in the reflecting direction of the apertured mirror 33. The 6-piece stop 38 and 6-piece prism 39 have the shapes shown in FIG. 5. They are in tight contact with each other.

When the eye refractive power of an object is to be measured, a light beam emitted from the measurement light source 37 is focused by the projection stop 36 and is primarily formed into an image in front of the objective lens 32 by the projection lens 35. This light beam is then transmitted through the objective lens 32 and dichroic mirror 31 and projected onto the pupil center of the eye E. This light beam is formed into an image at the eye fundus, and reflected light passes through a portion around the pupil and strikes the objective lens 32 again. The incident light beam thickens and is totally reflected by the apertured mirror 33. The reflected light beam is split into six light components by the 6-piece stop 38. These light components are refracted by the 6-piece prism 39 to be incident on the light-receiving area of the two dimensional image pickup element 41 within a proper range so as to project six spot images on the two dimensional image pickup element 41. The eye refractive power can be measured on the basis of the positional relationship between the six spot images on the two dimensional image pickup element 41.

An optical system for fixation target projection and a light-receiving optical system used for both anterior observation and alignment detection are arranged in the reflecting direction of the dichroic mirror 31. The light-receiving optical system includes a lens 42, dichroic mirror 43, prism stop 44 for alignment, imaging lens 45, and two dimensional image pickup element (two dimensional CCD) 46. The measurement light source 37 is also used as a light source with a wavelength of 880 nm for alignment detection. A light beam from the measurement light source 37 is reflected by the cornea of the eye E. The reflected light beam returns to the measurement unit 6 and is reflected by the dichroic mirror 31. This light beam then passes through the lens 42 and is reflected by the dichroic mirror 43 to be guided to the alignment optical system.

Figure 4:
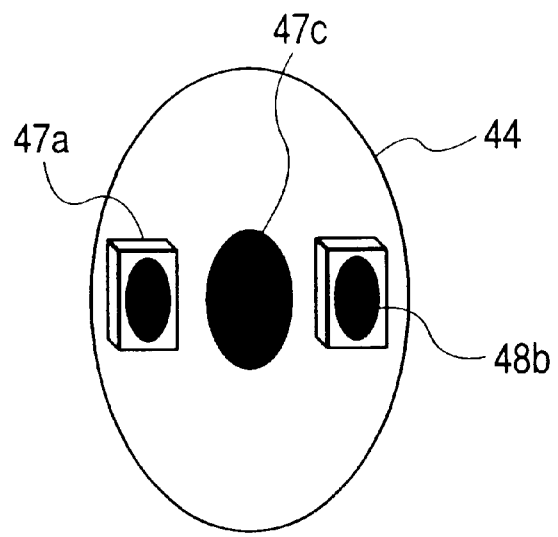
FIG. 4 is a view showing the arrangements of a 6-piece stop and 6-piece prism.

The alignment optical system includes the prism stop 44. FIG. 4 shows the structure of the prism stop 44. Three aperture portions are formed horizontally in a disk-like stop plate, and alignment prisms 47a and 47b which transmit only light beams with wavelengths near 880 nm are bonded to the surface of the stop plate which is located on the dichroic mirror 43 side. The light beam transmitted through the prism 47a is refracted downward, and the light beam transmitted through the prism 47b is refracted upward. The light beam that passes through a aperture portion 47c is transmitted therethrough without refraction. As a consequence, three luminescent points are formed on the two dimensional image pickup element 46 by the imaging lens 45. The reflected cornea images formed by extrinsic eye light sources 48a and 48b with a wavelength of 770 mn return to the measurement unit 6 and are reflected by the dichroic mirror 31, together with the anterior image. These light images pass through the lens 42 and are reflected by the dichroic mirror 43 to be guided to the alignment optical system. The light images then pass through only the aperture portion 47c in the center of the prism stop 44 and formed into images on the two dimensional image pickup element 46 by the imaging lens 45. An alignment state can be detected in the manner described later on the basis of the positional relationship between the luminescent points on the two dimensional image pickup element 46.

A fixation projection optical system will be described next. The fixation projection optical system is placed on the transmission side of the dichroic mirror 43. This system includes a total reflection mirror 49, fixation derivation lens 50, fixation chart 51, and fixation projection light source 52. At the time of fixation derivation, a projection light beam from the fixation projection light source 52 that is turned on illuminates the fixation chart 51 from the rear side and is projected onto the eye fundus of the eye E via the fixation derivation lens 50 and lens 42. The fixation derivation lens 50 can move in the optical axis direction upon rotation of the fixation derivation lens motor 61 so as to cope with changes in the visibility of the eye E.

Figure 8:
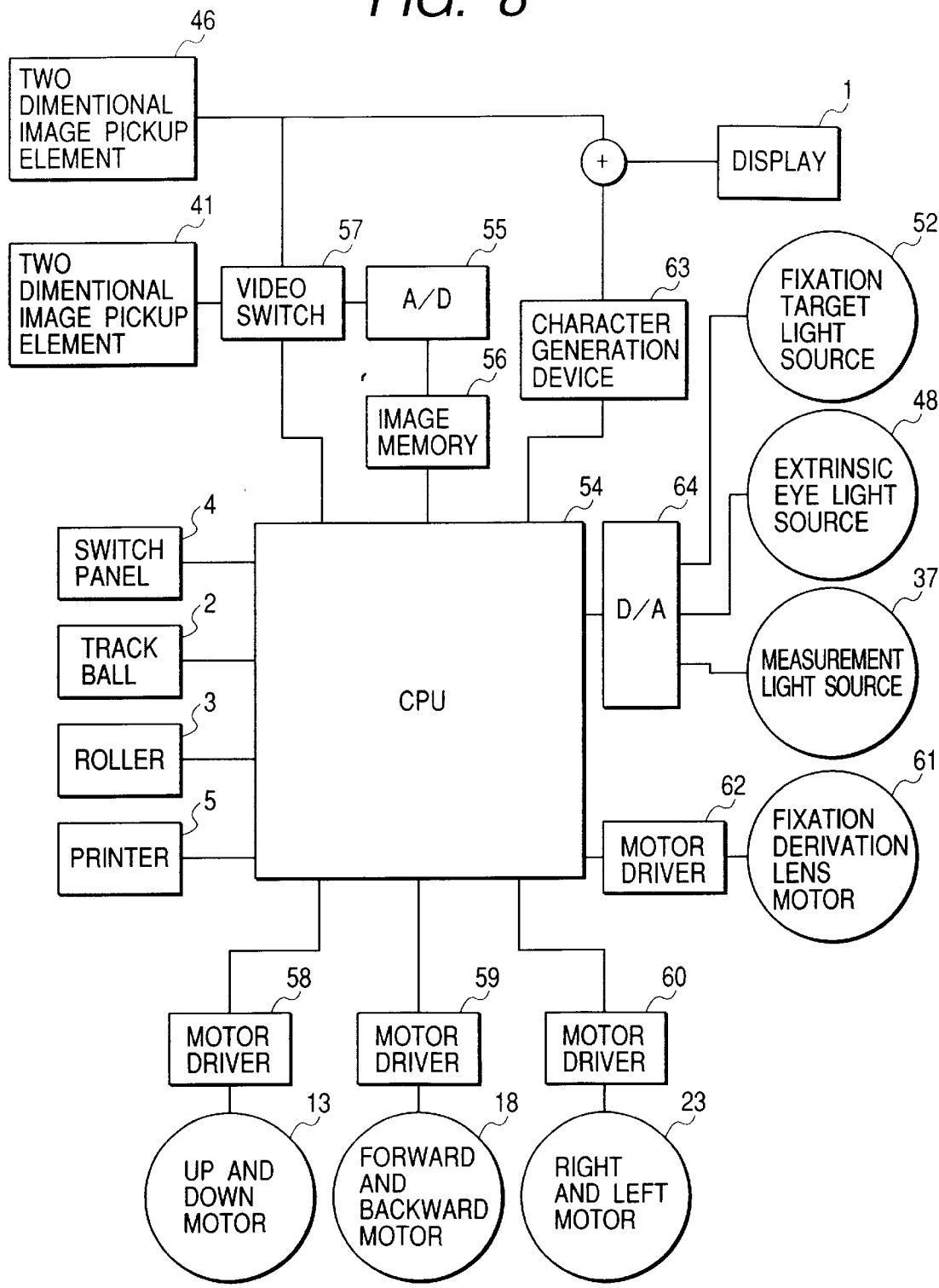
FIG. 8 is a block diagram showing an electric arrangement.

FIG. 8 is an electric block diagram showing the overall arrangement of the apparatus according to this embodiment. The switch panel 4 (including a measurement switch, print start switch, and the like), rotary encoders respectively incorporated in the track ball 2 and roller 3 which are used to roughly align the measurement unit with the eye, and the printer 5 for printing measurement results are connected to ports of a CPU 54 serving as a processor for controlling the overall apparatus and executing arithmetic processes. A video signal representing the eye fundus image picked up by the two dimensional image pickup element 41 is sent through a video switch 57 and converted into digital data by an A/D converter 55. This data is stored in an image memory 56. The CPU 54 computes eye refractive power on the basis of the image stored in the image memory 56. A video signal representing the anterior image picked up by the two dimensional image pickup element 46 is sent through the video switch 57 and converted into digital data by the A/D converter 55. This data is stored in the image memory 56. The CPU 54 performs image processing such as luminescent point image extraction and pupil extraction on the basis of the image stored in the image memory 56. The video signal representing the anterior image picked up by the two dimensional image pickup element 46 is synthesized with a signal from a character generation device 63 to display the anterior image and measured values on the display 1. The up and down motor 13, forward and backward motor 18, right and left motor 23, and fixation derivation lens motor 61 are respectively connected to motor drivers 58, 59, 60, and 62, and driven by command signals from the CPU 54. The fixation projection light source 52, an extrinsic eye light source 48, and the measurement light source 37 are connected to a D/A converter 64 through drivers (not shown), and can change the light amounts in accordance with instructions from the CPU 54.

Figures 6A, 6B, 6C:
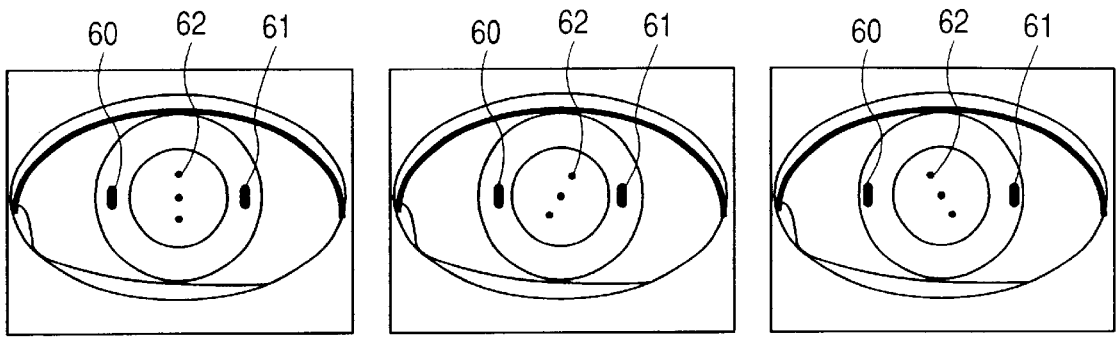
FIGS. 6A, 6B and 6C are views each showing an anterior image at the time of alignment based on reflected images of alignment light.

Each of FIGS. 6A to 6C shows an anterior image of an eye to be examined which is observed when position detection is accurately performed by using the reflected cornea image formed by the measurement light source 37 in alignment detection. FIG. 6A shows a case where alignment is properly performed in the forward-and-backward direction. The anterior image and the reflected cornea images from the extrinsic eye light sources 48a and 48b are transmitted through the aperture portion 47c in the center of the prism stop 44 and formed into luminescent points 60 and 61. Meanwhile, the reflected cornea image formed by the measurement light source 37 is formed into three vertically aligned luminescent points 62. The light beam transmitted through the aperture portion 47a (see FIG. 4) of the prism stop 44 is formed into the upper luminescent point, the light beam transmitted through the aperture portion 47b is formed into the lower luminescent point, and the light beam transmitted through the aperture portion 47c is formed into the middle luminescent point. FIG. 6B shows an observation image in a state where the distance between the eye E and the measurement unit 6 is larger (farther) than a proper value. In this state, a line connecting the three luminescent points 62 tilts clockwise. In contrast to this, FIG. 6C shows an observation image in a state where the distance between the eye E and the measurement unit 6 is smaller (nearer) than a proper value. In this state, a line connecting the three luminescent points 62 tilts counterclockwise. An alignment state in the forward-and-backward direction (Z direction) can be detected from the positions of the upper and lower luminescent points of the three luminescent points in the right-and-left direction (X-coordinates). An alignment state in the up-and-down and right-and-left directions (X and Y directions) can be detected from the position (coordinates) of the middle luminescent point.

Figures 7A, 7B, 7C:
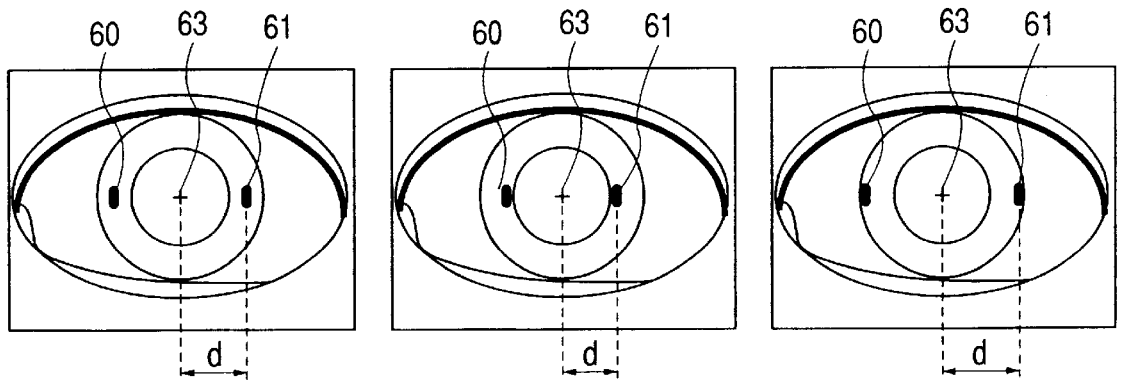
FIGS. 7A, 7B and 7C are views each showing an anterior image at the time of alignment based on reflected images of a pupil and extrinsic eye light.

Each of FIGS. 7A to 7C shows an anterior image of an eye to be examined which is observed when the reflected cornea image formed by the extrinsic eye light source 48 is used for alignment detection instead of the reflected cornea image formed by the measurement light source 37. FIG. 7A shows a case where alignment is properly performed in the forward-and-backward direction (Z direction). In this state, a distance d between the position of a pupil center 63 and a reflected cornea image 61 (or image 60) formed by the extrinsic eye light source 48 becomes a certain predetermined value. FIG. 7B shows an observation image in a state where the distance between the eye E and the measurement unit 6 is larger than a proper value. In this state, the distance d is smaller than that in the case shown in FIG. 7A. In contrast to this, FIG. 7C shows an observation image in a state where the distance between the eye E and the measurement unit 6 is smaller than the proper value. In this state, the distance d is larger than that in the case shown in FIG. 7A. Therefore, an alignment state in the Z direction can be detected from the value of the distance d. Alignment states in the X and Y directions can be detected from the position (coordinates) of the pupil center.

As described above, an alignment state in the forward-and-backward direction (Z direction) is calculated from the tilt of a line connecting three luminescent points (in the scheme shown in FIGS. 6A to 6C) or from the distance d between the pupil center and each luminescent point (in the scheme shown in FIGS. 7A to 7C). Not that the distance d varies depending on the radius of curvature of the cornea of an eye (variations among individuals), and hence is preferably corrected in accordance with the radius of curvature. In addition, an alignment state in the up-and-down and right-and-left directions (X and Y directions) is calculated from the coordinates (in the scheme shown in FIGS. 6A to 6C) of the central luminescent point or the position coordinates of the pupil center (in the scheme shown in FIGS. 7A to 7C). When the scheme shown in FIGS. 6A to 6C is compared with that shown in FIGS. 7A to 7C, the detectable ranges in the X, Y, and Z directions are wider in the scheme shown in FIGS. 7A to 7C. On the other hand, detection precisions in the X, Y, and Z directions are higher in the scheme shown in FIGS. 6A to 6C. That is, in the scheme shown in FIGS. 6A to 6C, the detection ranges are narrow, but high-precision position detection can be done. In contrast to this, in the scheme shown in FIGS. 7A to 7C, the detection ranges are wide but position detection is inferior in precision. The apparatus according to this embodiment therefore realizes an auto-alignment scheme that satisfies both the requirements for wide detection ranges and high detection precision by making the most of the merits of the respective schemes, as will be described later.

An operation procedure in the apparatus according to this embodiment will be described next. The face of an object to be examined is placed on the face rest (not shown). The operator then operates the track ball 2 and roller 3 to align the measurement unit 6 with the optical axis O of the eye E. The measurement unit 6 is moved right-and-left and forward-and-backward directions with respect to the eye by operating the track ball 2, and moved in the up-and-down direction by operating the roller 3, thereby aligning the measurement unit 6. In this operation, on the apparatus side, the CPU 54 receives output signals from the respective pulse counters and rotary encoders incorporated in the track ball 2 and roller 3 to detect the operation amount and speed. In accordance with the operation amount and speed, the CPU 54 drives the up and down motor 13, forward and backward motor 18, and right and left motor 23 through the respective motor drivers 58, 59, and 60.

The operator moves the measurement unit 6 with the above operation and checks an observation image of the eye E on the display 1. Upon checking the image, the operator presses the measurement start switch on the switch panel 4. In accordance with this operation, auto-alignment is started to automatically align the measurement unit 6 with the eye E. The flow chart shown in FIG. 9 shows a series of operations from the start of auto-alignment to the end.

Accurate alignment operation (fine alignment) based on a reflected cornea image of alignment light will be described first. In step S1, the image picked up by the two dimensional image pickup element 46 is stored in the image memory 56, and the CPU 54 detects three luminescent points of reflected cornea images formed by the measurement light source 37 by image processing. In step S2, it is checked whether the three luminescent points are detected in step S1. If YES in step S2, the flow advances to step S3, in which the CPU 54 calculates displacement amounts in the X, Y, and Z directions from the positions of the three luminescent points. In step S4, it is checked whether the displacement amounts in the X, Y, and Z directions calculated in step S3 fall within measurable ranges. If the displacement amounts fall within the measurable ranges, auto-alignment is complete. If the displacement amounts fall outside the measurable ranges, the flow advances to step S5. In step S5, the respective motors in the up-and-down, right-and-left, and forward-and-backward directions are driven by commands from the CPU 54 in accordance with the displacement amounts in the X, Y, and Z directions, thereby moving the measurement unit 6. The flow then return to step S1. This loop of steps S1 to S5 is repeated until it is determined in step S4 that the displacement amounts in the X, Y, and Z directions fall within the measurable ranges, thereby performing auto-alignment. When auto-alignment is complete, measurement of eye refractive power is executed.

Alignment operation (coarse alignment) to be done until the measurement unit 6 enters a range in which three luminescent points of reflected cornea images formed by the measurement light source 37 can be satisfactorily detected. This processing is performed when "NO" is obtained in step S2, i.e., three luminescent points are not detected. If it is determined in step S2 that three luminescent points are not detected, the flow advances to step S6, in which the CPU 54 detects the position (coordinates) of the pupil center of the eye by image processing on the basis of the image picked up by the two dimensional image pickup element 46 and stored in the image memory 56. The CPU 54 then calculates displacement amounts in the X and Y directions from the detected pupil center position. In step S7, it is checked whether the displacement amounts in the X and Y directions obtained in step S6 fall within predetermined ranges. If NO in step S7, the flow advances to step S8. The predetermined ranges are the ranges in the X and Y directions in which three luminescent points of reflected cornea images formed by the measurement light source 37 can be satisfactorily detected. In step S8, the up and down motor and right and left motor are driven by commands from the CPU 54 in accordance with the displacement amounts in the X and Y directions, thereby moving the measurement unit 6. The flow then returns to step S6 again. This loop of steps S6 to S8 is repeated until it is determined in step S7 that the displacement amounts in the X and Y directions fall within the predetermined ranges. The following is the reason why alignment in the Z direction is not performed in the processing loop of steps S6 to S8. As described above with reference to FIGS. 7A to 7C, a displacement amount in the Z direction can be detected from the distance between the pupil center and each luminescent point. Since this distance varies depending on the radius of curvature of the cornea, the displacement amount detected in the Z direction varies among patients. For this reason, in spite of the fact that the displacement amount in the Z direction is small (e.g., in a case where after measurement for one of the left and right eyes is completed, measurement is switched to the other eye), it may be determined that the error in the Z direction is large. If the measurement unit is driven on the basis of this determination, the displacement amount in the Z direction may be increased. Assume that the main reason why three luminescent points of reflected cornea images formed by the measurement light source 37 cannot be detected in step S1 is the displacement amounts in the X and Y directions. In this case, if alignment in the Z direction is performed, together with alignment in the X and Y directions, the displacement amount in the Z direction may increase. In order to prevent this, alignment in the Z direction is not performed in steps S6 to S8, but alignment in only the X and Y direction is performed.

If YES in step S7, the flow advances to step S9. The processing in steps S9 and S10 is the same as that in steps S1 and S2 described above. That is, three luminescent points of reflected cornea images formed by the measurement light source 37 are detected. It is checked in step S10 whether three luminescent points are detected in step S7. If YES in step S10, the flow advances to step S3. In this case, the operation in step S4 and the subsequent steps is performed in the above manner.

If NO in step S10, the flow advances to step S11. The processing in step S11 and the subsequent steps is characterized in that alignment is performed upon detection of a displacement amount in the Z direction, as compared with the processing in steps S6 to S8 described above. The CPU 54 detects the position of the pupil center and the central position of a reflected cornea image formed by the extrinsic eye light source 48 by image processing on the basis of the image picked up by the two dimensional image pickup element 46 and stored in the image memory 56. The CPU 54 then calculates the distance between the detected pupil center and the detected reflected cornea image center to obtain a displacement amount in the Z direction as well as displacement amounts in the X and Y directions. More specifically, displacement amounts in the X and Y directions are detected on the basis of the coordinate values of the pupil center, and a displacement amount in the Z direction is detected from the distance between the reflected extrinsic eye light image and the pupil center. According to another method, displacement amounts in the X, Y, and Z directions can be obtained from the distance between two reflected cornea images (images 60 and 61 in FIGS. 7A to 7C) formed by the extrinsic eye light source 48 or the coordinate values of these images without obtaining a pupil center position.

In step S12, it is checked whether the displacement amounts in the X, Y, and Z directions obtained in step S11 fall within predetermined ranges. If NO in step S12, the flow advances to step S13. The predetermined ranges are the ranges in the X, Y, and Z directions in which three luminescent points of reflected cornea images formed by the measurement light source 37 can be satisfactorily detected. In step S13, the motors in the respective directions are driven by instructions from the CPU 54 in accordance with the displacement amounts, thereby moving the measurement unit 6. The flow then returns to step S11 again. This loop of steps S11 to S13 is repeated until it is determined in step S12 that the displacement amounts fall within the predetermined ranges. If YES in step S13, the flow advances to step S1. With the above processing, all the displacement amounts in the X, Y, and Z directions have already fallen within the range in which three luminescent points of reflected cornea images formed by the measurement light source 37 can be satisfactorily detected. In step S2, therefore, three luminescent point of reflected cornea images can be detected. After this step, auto-alignment is performed in the above manner. When auto-alignment is complete, measurement of eye refractive power is executed.

The procedure for auto-alignment in FIG. 9 is an algorithm which includes the first alignment mode (steps S1 to S5) for performing final fine alignment, the second alignment mode (steps S6 to S8) for performing coarse article in the X and Y directions, and the third alignment mode (steps S11 to S13) for performing coarse alignment including alignment in the Z direction as well, and sequentially executes the three modes. According to a modification of this embodiment, the above procedure may be modified into an algorithm in which the second alignment mode is omitted, i.e., if NO in step S2, the flow advances to step S11.

As described above, alignment based on accurate position detection with a narrow detection range may be organically combined with alignment with a wide detection range and lower position detection precision to make the most of the merits of the two alignment techniques, thereby realizing auto-alignment that satisfies both the requirements for a wider detection range and higher detection position.

According to the present invention, there is provided an ophthalmologic apparatus which can perform auto-alignment with a wide detection range with respect to eyes to be examined and high detection precision.

What is claimed is:

1. An ophthalmologic apparatus comprising:
   (1) a movable measurement unit which includes a measurement optical system for measuring an eye to be examined;
   (2) a first light source which irradiates the eye with first light from a direction different from that of an optical axis of said measurement optical system;
   (3) a second light source which irradiates the eye with second light from an optical axis direction of said measurement optical system;
   (4) image pickup means for obtaining image information of the eye;
   (5) first detection means for detecting a positional relationship between said measurement unit and the eye on the basis of information of the first reflected cornea image formed by said first light source on the basis of image information from said image pickup means; and
   (6) second detection means for detecting a positional relationship between said measurement unit and the eye on the basis of information of the second reflected cornea image formed by said second light source on the basis of image information from said image pickup means,
   wherein said measurement unit is driven to be aligned with the eye on the basis of a detection result formed by said first detection means when said second detection means does not detect the positional relationship between said measurement unit and the eye.

2. An apparatus according to claim 1, further comprising:
   (1) pupil position detection means for obtaining a position of a pupil on the basis of image information from said image pickup means; and
   (2) further detection means for detecting a positional relationship between said measurement unit and the eye on the basis of pupil position information detected by said pupil position detection means.

3. An apparatus according to claim 1, further comprising control means for performing control to align said measurement unit with the eye on the basis of a detection result obtained by said second detection means after aligning said measurement unit with the eye on the basis of a detection result obtained by said first detection means.

4. An apparatus according to claim 3, wherein when a positional relationship between said measurement unit and the eye cannot be detected by said second detection means, said control means controls said measurement unit to align said measurement unit with the eye on the basis of a detection result obtained by said second detection means after driving said measurement unit on the basis of a detection result obtained by said first detection means.

5. An apparatus according to claim 1, wherein said unit can move in up-and-down, right-and-left, and forward-andbackward directions with respect to the eye, said first detection means performs position detection in the up-and-down, right-and-left, and forward-and-backward directions, and said second detection means performs at least detection in the forward-and-backward direction.

6. An apparatus according to claim 1, wherein each of said first and second detection means includes a process which processes the image information and computes a positional relationship between said measurement unit and the eye.

7. An auto-alignment method for an ophthalmologic apparatus including a measurement optical system which measures an eye to be examined, an illumination system which illuminates the eye with extrinsic eye light, and an image pickup device to obtain image information of the eye, comprising:
   (1) the detection step of irradiating the eye with a light beam through the measurement optical system, and detecting a reflected cornea image of the light beam on the basis of the image information;
   (2) the aligning step of, when a reflected cornea image can be detected in the detection step, aligning the measurement optical system with the eye on the basis of the reflected cornea image; and
   (3) the step of, when no reflected cornea image can be detected in the detection step, detecting a reflected cornea image based on the illumination of extrinsic eye light from the image information, aligning the measurement optical system in accordance with the reflected cornea image, and then performing the detection step again.

8. An auto-alignment method for an ophthalmologic apparatus including a measurement optical system which measures an eye to be examined, an illumination system which illuminates the eye with extrinsic eye light, and image pickup means for obtaining image information of the eye, comprising:
   (1) the detection step of irradiating the eye with a light beam through the measurement optical system, and detecting a reflected cornea image of the light beam on the basis of the image information from the image pickup means;
   (2) the first aligning step of, when a reflected cornea image can be detected in the detection step, aligning the measurement optical system with the eye on the basis of the reflected cornea image;
   (3) the second aligning step of, when no reflected cornea image can be detected in the detection step, detecting a pupil image of the eye, aligning the measurement optical system in accordance with the pupil image, and then shifting the detection step; and
   (4) the third aligning step of, when the reflected cornea image cannot be detected even after the second aligning step, detecting a reflected cornea image based on the illumination of extrinsic eye light on the basis of image information from the image pickup means, aligning the measurement optical system in accordance with the reflected cornea image, and then shifting to the detection step.

9. A method according to claim 7, wherein the reflected cornea image formed by the illumination of extrinsic eye light and a pupil position are detected, and the alignment is executed on the basis of a positional relationship between the reflected cornea image and the pupil position.

10. A method according to claim 8, wherein in the first aligning step, alignment in up-and-down, right-and-left, and forward-and-backward directions is executed, in the second aligning step, alignment in the up-and-down and right-and-left directions is executed, and in the third aligning step, at least alignment in the forward-and-backward direction is executed.

11. An auto-alignment method for an ophthalmologic apparatus including a measurement optical system which measures an eye to be examined, and image pickup means for obtaining image information of the eye, comprising:
   (1) the detection step of irradiating the eye with a light beam through the measurement optical system, and detecting a reflected cornea image of the light beam on the basis of the image information from the image pickup means;
   (2) the aligning step of, when a reflected cornea image can be detected in the detection step, aligning the measurement optical system with the eye on the basis of the reflected cornea image; and
   (3) the step of, when no reflected cornea image can be detected in the detection step, detecting a pupil image of the eye on the basis of an image signal from the image pickup means, aligning the measurement optical system in accordance with the pupil image, and performing the detection step again.

12. An auto-alignment method for an ophthalmologic apparatus including a measurement optical system which measures an eye to be examined, and image pickup means for obtaining image information of the eye, comprising:
   (1) the detection step of irradiating the eye with a light beam through the measurement optical system, and detecting a reflected cornea image on the basis of image information from the image pickup means;
   (2) the first aligning step of, when a reflected cornea image can be detected in the detection step, aligning the measurement optical system with the eye on the basis of a position of the eye which is discriminated based on the reflected cornea image;
   (3) the second aligning step of, when no reflected cornea image can be detected in the detection step, detecting a pupil image of the eye on the basis of image information from the image pickup means, aligning the measurement optical system in accordance with the pupil image, and then shifting to the detection step; and
   (4) the third aligning step of, when the reflected cornea image cannot be detected even after the second aligning step, detecting the reflected cornea image on the basis of the image information from the image pickup means, aligning the measurement optical system in accordance with the reflected cornea image, and then shifting the detection step.

13. A method according to claim 8, wherein the reflected cornea image formed by the illumination of extrinsic eye light and a pupil position are detected, and the alignment is executed on the basis of a positional relationship between the reflected cornea image and the pupil position.

14. A method according to claim 9, wherein in the first aligning step, alignment in up-and-down, right-and-left, and forward-and-backward directions is executed, in the second aligning step, alignment in the up-and-down and right-and-left directions is executed, and in the third aligning step, at least alignment in the forward-and-backward direction is executed.

15. An ophthalmologic apparatus comprising:
   (1) a movable measurement unit which includes a measurement optical system for measuring an eye to be examined;
   (2) a first light source which irradiates the eye with first light from a direction different from that of an optical axis of said measurement optical system;
   (3) a second light source which irradiates the eye with second light from an optical axis direction of said optical measurement optical system;

(4) image pickup means for obtaining image information of the eye;

(5) first detection means for detecting a positional relationship between said measurement unit and the eye on the basis of information of the first reflected cornea image formed by said first light source on the basis of image information from said image pickup means;

(6) second detection means for detecting a positional relationship between said measurement unit and the eye on the basis of information of the second reflected cornea image formed by said second light source on the basis of image information from said image pickup means;

(7) pupil position detection means for obtaining a position of a pupil on the basis of image information from said image pickup means; and (8) third detection means for detecting a positional relationship between said measurement unit and the eye on the basis of pupil position information detected by said pupil position detection means, wherein said measurement unit is driven to be aligned with the eye on the basis of one of detection results formed by sequentially changing over said first detection means, second detection means, and third detection means.

* * * * *